United States Patent
Weber et al.

(10) Patent No.: US 11,576,614 B2
(45) Date of Patent: Feb. 14, 2023

(54) BANDAGE\E-TATTOO COMBINATION

(71) Applicant: Boston Scientific Scimed Inc., Maple Grove, MN (US)

(72) Inventors: Jan Weber, Maastricht (NL); Jeffrey E. Stahmann, Ramsey, MN (US); Keith R. Maile, New Brighton, MN (US); James M. Peck, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 663 days.

(21) Appl. No.: 16/656,349

(22) Filed: Oct. 17, 2019

(65) Prior Publication Data

US 2020/0121252 A1 Apr. 23, 2020

Related U.S. Application Data

(60) Provisional application No. 62/747,544, filed on Oct. 18, 2018.

(51) Int. Cl.
*A61B 5/00* (2006.01)
*A61B 5/1455* (2006.01)

(52) U.S. Cl.
CPC .......... *A61B 5/6843* (2013.01); *A61B 5/1455* (2013.01); *A61B 5/6833* (2013.01); *A61B 2562/12* (2013.01); *A61B 2562/164* (2013.01)

(58) Field of Classification Search
CPC ... A61B 5/0205; A61B 5/1455; A61B 5/0059; A61B 5/14551; A61B 5/14552;

(Continued)

(56) References Cited

U.S. PATENT DOCUMENTS 6,978,182 B2 12/2005 Mazar et al.
8,515,511 B2 * 8/2013 Boutelle ............ A61B 5/14552
600/323

(Continued)

FOREIGN PATENT DOCUMENTS

WO WO-2010107913 A2 * 9/2010 ......... A61B 5/04085

OTHER PUBLICATIONS

Garry, B., & Shafir, E. (2012). Optical methods for distance and displacement measurements. Advances in Optics and Photonics, 4:441-471.

*Primary Examiner* — Chu Chuan Liu
(74) *Attorney, Agent, or Firm* — Faegre Drinker Biddle & Reath LLP

(57) ABSTRACT

Embodiments disclosed herein relate to devices and methods for monitoring one or more physiological parameters of a subject. In an embodiment, a wearable device comprises a substrate configured to attached to a subject's skin. The substrate comprises a middle portion arranged between two end portions, wherein the middle portion is more flexible than at least one of the end portions. The wearable device also comprises a physiological sensor arranged on the middle portion. The physiological sensor is configured to sense a physiological signal of the subject when the wearable device is attached to the subject's skin. And, the wearable device comprises one or more electrical components arranged on at least one of the end portions, wherein at least one of the one or more electrical components is coupled to the physiological sensor.

20 Claims, 5 Drawing Sheets

(58) Field of Classification Search
CPC ..... A61B 5/145; A61B 5/14532; A61B 5/318; A61B 5/30; A61B 5/0803; A61B 5/6801; A61B 5/6802; A61B 5/681; A61B 5/6813; A61B 5/6823; A61B 5/6824; A61B 5/6825; A61B 5/6826; A61B 5/6828; A61B 5/6829; A61B 5/6843; A61B 5/6833; A61B 2562/164; A61B 2562/12

See application file for complete search history.

(56) References Cited

U.S. PATENT DOCUMENTS

| | | | |
|---|---|---|---|
| 9,609,921 B1* | 4/2017 | Feinstein | A44C 5/2071 |
| 2004/0127958 A1 | 7/2004 | Mazar et al. | |
| 2010/0025238 A1* | 2/2010 | Gottlieb | A61B 5/14532 |
| | | | 204/403.01 |
| 2011/0245633 A1* | 10/2011 | Goldberg | A61B 5/681 |
| | | | 600/323 |
| 2014/0378777 A1* | 12/2014 | Conrad | A61B 5/1455 |
| | | | 600/301 |
| 2015/0313542 A1* | 11/2015 | Goldberg | A61B 5/6824 |
| | | | 368/282 |
| 2018/0271393 A1* | 9/2018 | Lee | A61B 5/6833 |

* cited by examiner

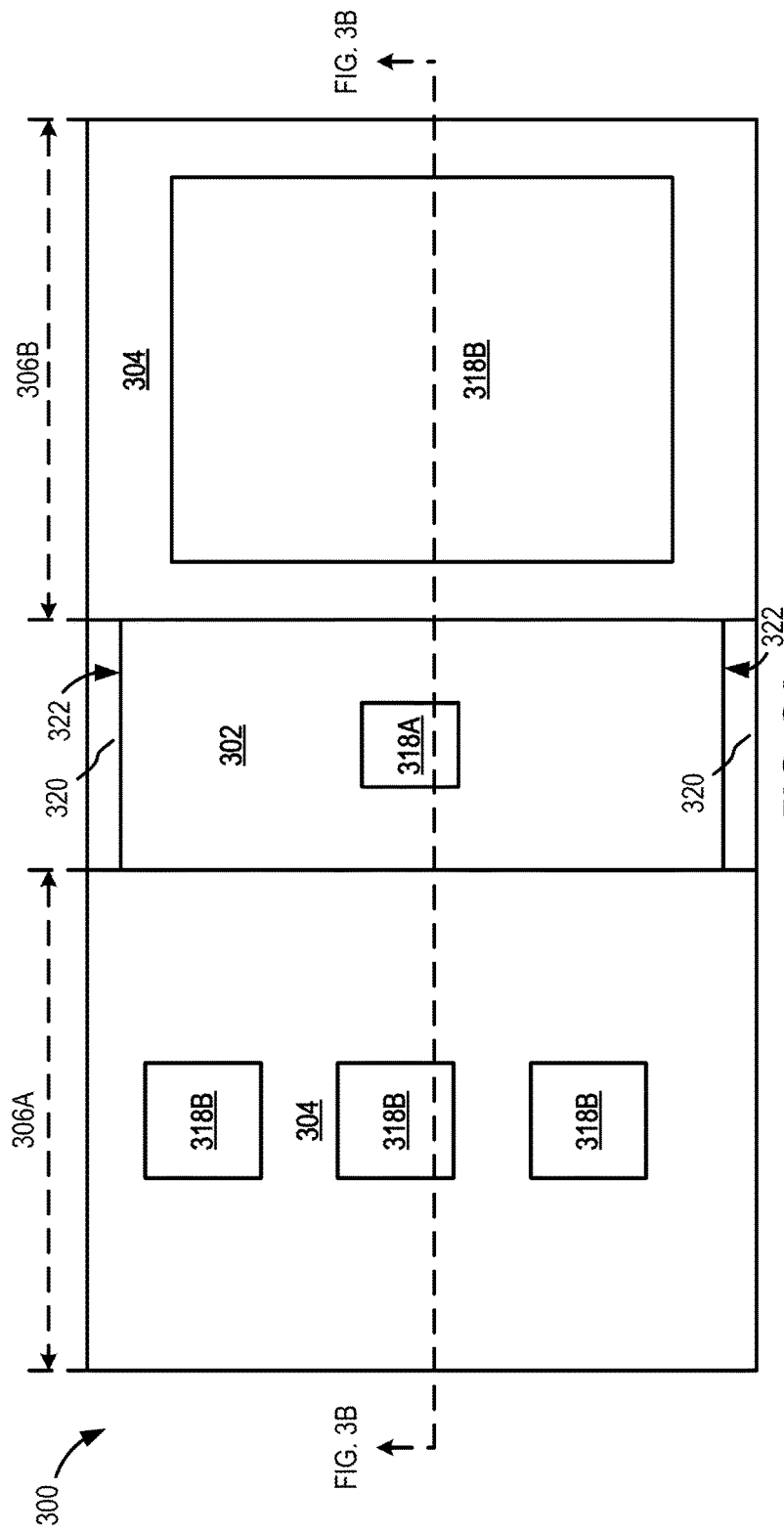
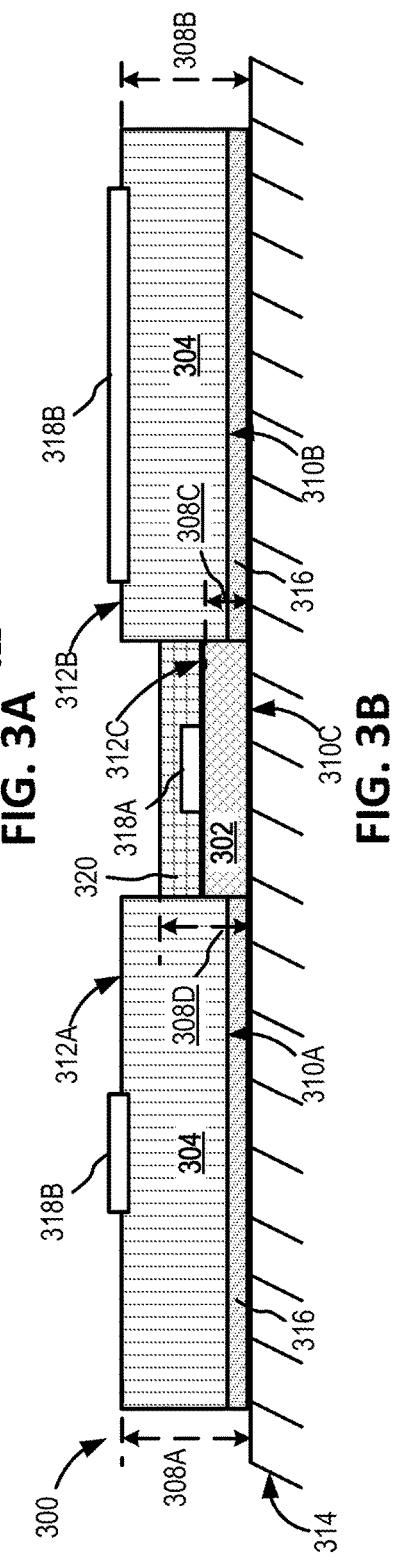

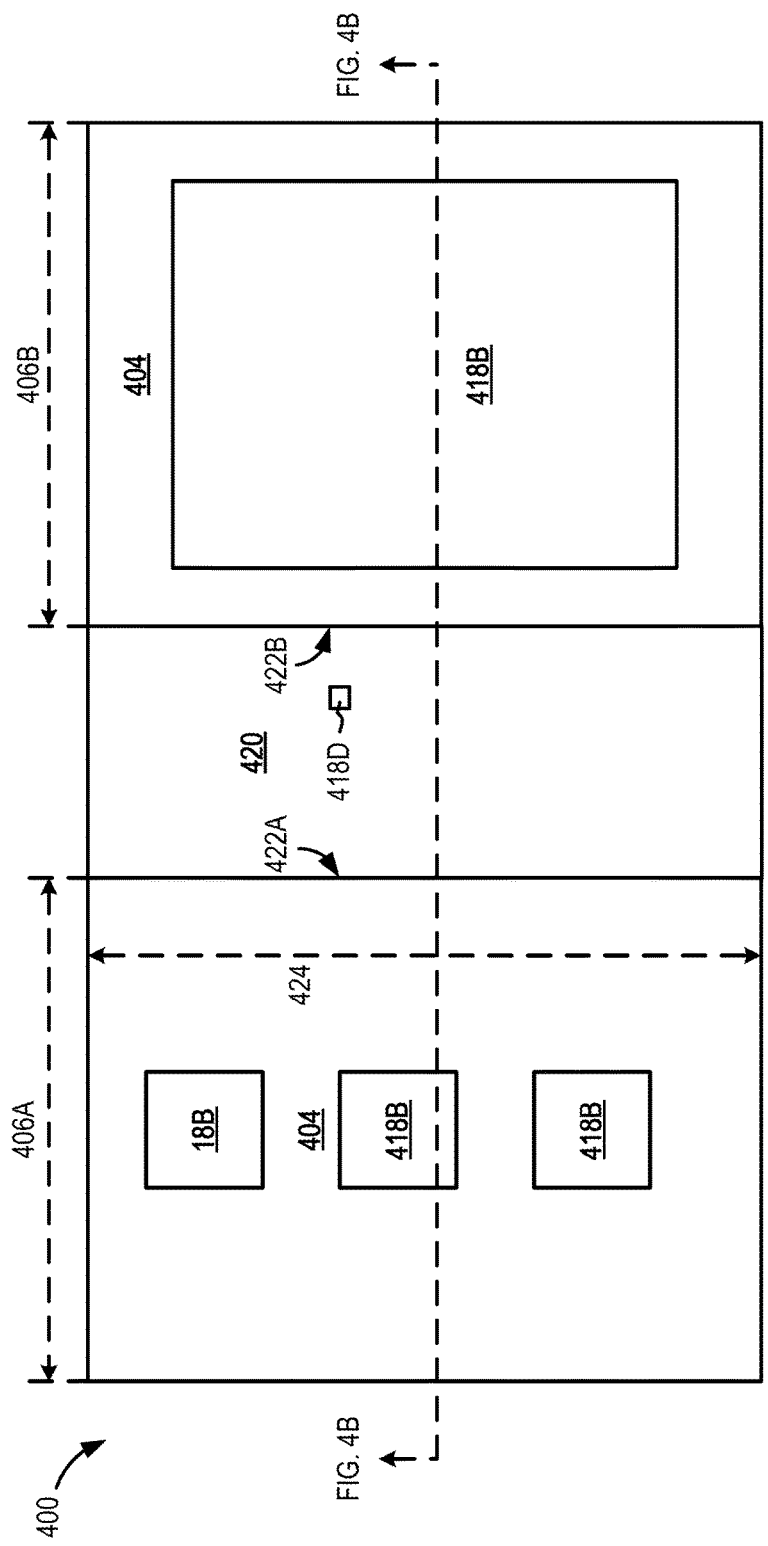
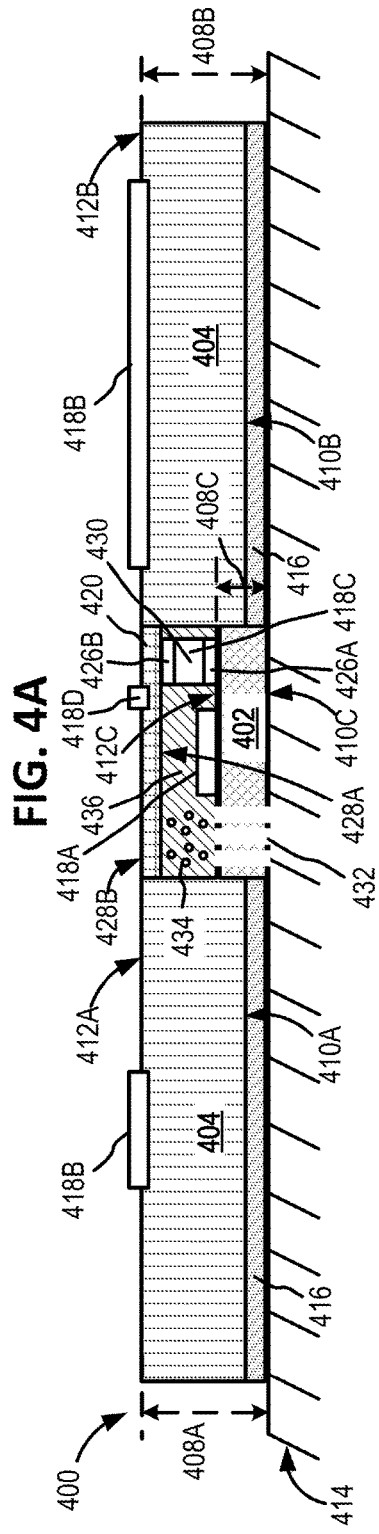

BANDAGE\E-TATTOO COMBINATION

CROSS-REFERENCE TO RELATED APPLICATION

This application claims priority to Provisional Application No. 62/747,544, filed Oct. 18, 2018, which is herein incorporated by reference in its entirety.

TECHNICAL FIELD

The present disclosure relates to devices and methods for monitoring one or more physiological parameters of a subject. More specifically, the disclosure relates to devices, systems, and methods for monitoring one or more physiological parameters of a subject using a wearable device.

BACKGROUND

Wearable physiological monitoring systems may provide certain benefits over other non-wearable devices. For example, wearable systems may include one or more sensors that can provide more accurate sensing and data due to their contact with a subject and/or location on a subject.

SUMMARY

Wearable devices for monitoring one or more physiological parameters of a subject are disclosed. Exemplary wearable devices include but are not limited to the following examples.

In an Example 1, a wearable device is configured to be attached to a subject's skin, the wearable device comprises: a substrate configured to attached to a subject's skin, the substrate comprising a middle portion arranged between two end portions, wherein the middle portion is more flexible than at least one of the end portions; a physiological sensor arranged on the middle portion, the physiological sensor configured to sense a physiological signal of the subject when the wearable device is attached to the subject's skin; and one or more electrical components arranged on at least one of the end portions, wherein at least one of the one or more electrical components is coupled to the physiological sensor.

In an Example 2, the wearable device of Example 1, wherein at least the middle portion is stretchable.

In an Example 3, the wearable device of any one of Examples 1-2, wherein the thickness of the middle portion is less than or equal to 10 micrometers.

In an Example 4, the wearable device of any one of Examples 1-3, further comprising a bridge portion connecting the end portions, wherein the bridge portion is less flexible than the middle portion.

In an Example 5, the wearable device of Example 4, wherein the bridge portion is arranged distal to and spaced apart from the middle portion.

In an Example 6, the wearable device of Example 5, wherein a gel is arranged between the bridge portion and the middle portion, the gel being configured to facilitate separation between the middle portion and bridge portion.

In an Example 7, the wearable device of any one of Examples 5-6, further comprising a capacitor arranged between the bridge portion and the middle portion, the capacitor being configured to measure a pressure on the wearable device.

In an Example 8, the wearable device of any one of Examples 5-7, wherein the bridge portion is opaque to at least one of visible light and ultraviolet light.

In an Example 9, the wearable device of any one of Examples 5-8, further comprising one or more optical components arranged on the bridge portion, the one or more optical components configured to emit light toward the middle portion, wherein at least one of: (i) a physiological parameter of the subject and (ii) a parameter of the wearable device is determined based on a reflected portion of the emitted light.

In an Example 10, the wearable device of any one of Examples 1-9, further comprising an adhesive disposed on proximal surfaces of the end portions, the adhesive configured to attach the wearable device to the subject's skin.

In an Example 11, the wearable device of any one of Examples 1-10, wherein the middle portion is porous to an active pharmaceutical ingredient.

In an Example 12, the wearable device of any one of Examples 1-11, wherein the middle portion is translucent to light having a wavelength between 600 nanometers and 1000 nanometers.

In an Example 13, a method of manufacturing a wearable device configured to be attached to a subject's skin, the method comprises: arranging a physiological sensor on a middle portion of a substrate, wherein the middle portion is between end portions of the substrate, the middle portion of the substrate being more flexible than at least one of the end portions and the physiological sensor configured to sense a physiological signal of the subject when the wearable device is attached to the subject's skin; arranging one or more electrical components on at least one the end portions, wherein at least one of the one or more electrical components are electrically connected to the physiological sensor; and connecting the end portions using one or more bridge portions.

In an Example 14, the method of Example 13, wherein the bridge portion is arranged distal to and spaced apart from the middle portion.

In an Example 15, the method of any one of Examples 13-14, further comprising arranging one or more optical components on the bridge portion, the one or more optical components configured to emit light toward the middle portion, wherein at least one of: (i) a physiological parameter of the subject and (ii) a parameter of the wearable device is determined based on a reflected portion of the emitted light.

In an Example 16, a wearable device is configured to be attached to a subject's skin, the wearable device comprises: a substrate configured to attached to a subject's skin, the substrate comprising a middle portion arranged between two end portions, wherein the middle portion is arranged between the end portions, wherein the middle portion is more flexible than at least one of the end portions; a physiological sensor arranged on the middle portion, the physiological sensor configured to sense a physiological signal of the subject when the wearable device is attached to the subject's skin; and one or more electrical components arranged on at least one of the end portions, wherein at least one of the one or more electrical components is coupled to the physiological sensor.

In an Example 17, the wearable device of Example 16, wherein at least the middle portion is stretchable.

In an Example 18, the wearable device of Example 16, wherein the thickness of the middle portion is less than or equal to 10 micrometers.

In an Example 19, the wearable device of Example 16, further comprising a bridge portion connecting the end portions, wherein the bridge portion is less flexible than the middle portion.

In an Example 20, the wearable device of Example 19, wherein the bridge portion is arranged distal to and spaced apart from the middle portion.

In an Example 21, the wearable device of Example 20, wherein a gel is arranged between the bridge portion and the middle portion, the gel being configured to facilitate separation between the middle portion and bridge portion.

In an Example 22, the wearable device of Example 20, further comprising a capacitor arranged between the bridge portion and the middle portion, the capacitor being configured to measure a pressure on the wearable device.

In an Example 23, the wearable device of Example 20, wherein the bridge portion is opaque to at least one of visible light and ultraviolet light.

In an Example 24, the wearable device of Example 20, further comprising one or more optical components arranged on the bridge portion, the one or more optical components configured to emit light toward the middle portion, wherein at least one of: (i) a physiological parameter of the subject and (ii) a parameter of the wearable device is determined based on a reflected portion of the emitted light.

In an Example 25, the wearable device of Example 16, further comprising an adhesive disposed on proximal surfaces of the end portions, the adhesive configured to attach the wearable device to the subject's skin.

In an Example 26, the wearable device of Example 16, wherein the middle portion is porous to an active pharmaceutical ingredient.

In an Example 27, the wearable device of Example 16, wherein the middle portion is translucent to light having a wavelength between 600 nanometers and 1000 nanometers.

In an Example 28, a method of manufacturing a wearable device configured to be attached to a subject's skin, the method comprises: arranging a physiological sensor on a middle portion of a substrate, wherein the middle portion is between end portions of the substrate, the middle portion of the substrate being more flexible than at least one of the end portions and the physiological sensor configured to sense a physiological signal of the subject when the wearable device is attached to the subject's skin; arranging one or more electrical components on at least one the end portions, wherein at least one of the one or more electrical components are electrically connected to the physiological sensor; and connecting the end portions using one or more bridge portions.

In an Example 29, the method of Example 28, wherein the bridge portion is less flexible than the middle portion.

In an Example 30, the method of Example 28, wherein the bridge portion is arranged distal to and spaced apart from the middle portion.

In an Example 31, the method of Example 28, further comprising disposing a gel on the middle portion, the gel being configured to facilitate separation between the middle portion and bridge portion.

In an Example 32, the method of Example 28, further comprising arranging a capacitor between the bridge portion and the middle portion, the capacitor being configured to measure a pressure on the wearable device.

In an Example 33, the method of Example 28, wherein the bridge portion is opaque to at least one of visible light and ultraviolet light.

In an Example 34, the method of Example 28, further comprising disposing an adhesive on the end portions.

In an Example 35, the method of Example 28, further comprising arranging one or more optical components on the bridge portion, the one or more optical components configured to emit light toward the middle portion, wherein at least one of: (i) a physiological parameter of the subject and (ii) a parameter of the wearable device is determined based on a reflected portion of the emitted light.

While multiple embodiments are disclosed, still other embodiments of the present disclosure will become apparent to those skilled in the art from the following detailed description, which shows and describes illustrative embodiments of the subject matter disclosed herein. Accordingly, the drawings and detailed description are to be regarded as illustrative in nature and not restrictive.

BRIEF DESCRIPTION OF THE DRAWINGS

FIGS. 3A-3B are schematic illustrations of an exemplary wearable device, in accordance with embodiments of the disclosure.

FIGS. 4A-4B are schematic illustrations of another exemplary wearable device, in accordance with embodiments of the disclosure.

Figure 1:
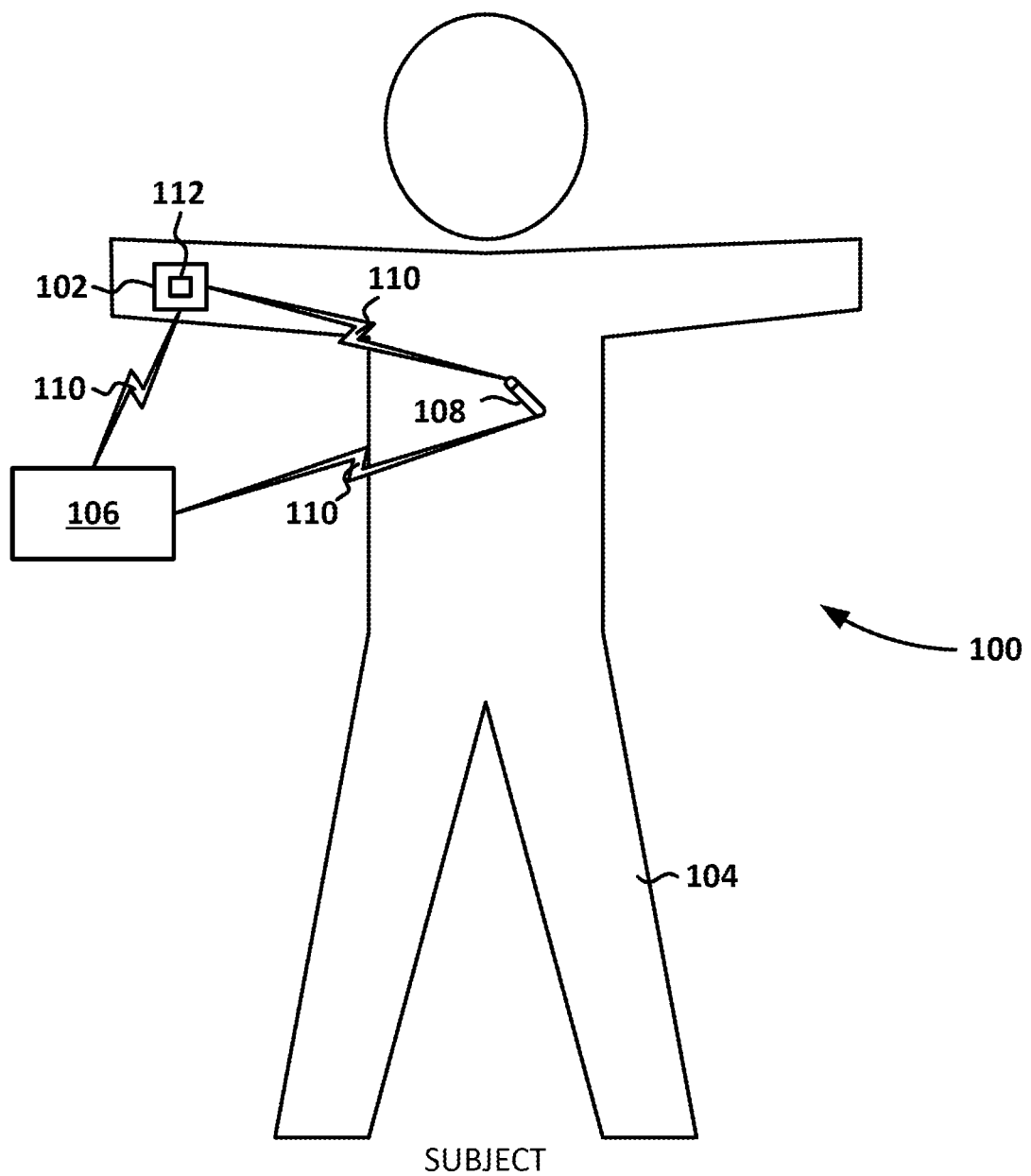
FIG. 1 is a schematic illustration of a medical system including a wearable device, in accordance with embodiments of the disclosure.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended pirs.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

The terms "up," "upper," and "upward," and variations thereof, are used throughout this disclosure for the sole purpose of clarity of description and are only intended to refer to a relative direction (i.e., a certain direction that is to be distinguished from another direction), and are not meant to be interpreted to mean an absolute direction. Similarly, the terms "down," "lower," and "downward," and variations thereof, are used throughout this disclosure for the sole purpose of clarity of description and are only intended to refer to a relative direction that is at least approximately opposite a direction referred to by one or more of the terms "up," "upper," and "upward," and variations thereof.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

For a wearable device to be directly connected to a subject and stay attached for a number of days or even weeks, the wearable device may be thin, flexible and stretchable. For that reason, thin substrates (e.g., below 10 micrometer), meandering conductive traces, and thinned-down silicon chips may be utilized. A potential drawback of such a construction is that the wearable device may become fragile, difficult to handle and construct. On the other hand, complex circuits, including sensors, communication elements, processors and power sources, may require a robust platform such as a "thick" substrate with plenty of surface area.

Embodiments disclosed herein address these problems, and others, by disclosing a wearable device including a middle portion arranged between two thicker, end portions. Additionally or alternatively, one or more sensors may be arranged on the middle portion allowing intimate contact with the subject and facilitating measuring physiological parameters of the subject while heavier electronic components may be arranged on the thicker, end portions, thereby facilitating a more durable construction of the wearable device. In embodiments, the thicker, end portions may be connected by a bridge portion, thereby increasing the durability of the wearable device.

FIG. 1 is a schematic illustration of a system 100 including a wearable device 102 arranged on a subject 104, in accordance with embodiments of the disclosure. The wearable device 102 may be positioned adjacent the body of a subject 104 and/or disposed on the body of the subject 104. The subject 104 may be a human, a dog, a pig, and/or any other animal having physiological parameters that can be recorded. For example, in embodiments, the subject 104 may be a human patient.

In addition to the wearable device 102, the system 100 may include one or more other devices 106, 108. In embodiments, the devices 106, 108 may be configured to be positioned adjacent the body of a subject 104, disposed on the body of the subject 104, and/or spaced apart from the subject 104. In embodiments, one or more of the devices 106, 108 may be implanted within the body of a subject 104.

In embodiments, the wearable device 102 and one or more of the devices 106, 108 may be communicatively coupled via a communication link 110. In embodiments, the communication link 110 may be, or include, a wired link (e.g., a link accomplished via a physical connection) and/or a non-wired communication link such as, for example, a short-range radio link, such as Bluetooth, Bluetooth Low Energy, IEEE 802.11, near-field communication (NFC), WiFi, a proprietary wireless protocol, and/or the like. The term "communication link" may refer to an ability to communicate some type of information in at least one direction between at least two devices, and should not be understood to be limited to a direct, persistent, or otherwise limited communication channel. That is, according to embodiments, the communication link 110 may be a persistent communication link, an intermittent communication link, an ad-hoc communication link, and/or the like. The communication link 110 may refer to direct communications between the wearable device 102 and one or more of the devices 106, 108, and/or indirect communications that travel between the wearable device 102 and one or more of the devices 106, 108 via at least one other device (e.g., a repeater, router, hub, and/or the like). The communication link 110 may facilitate uni-directional and/or bi-directional communication between wearable device 102 and one or more of the devices 106, 108. Data and/or control signals may be transmitted between the wearable device 102 and one or more of the devices 106, 108. In embodiments, subject data may be downloaded from one or more of the wearable device 102 and the devices 106, 108 periodically or on command. The clinician and/or the subject 104 may communicate with the wearable device 102 and one or more of the devices 106, 108, for example, to acquire subject data or to initiate, terminate and/or modify recording and/or therapy. In embodiments, the communication link 110 may facilitate encryption and/or other methods to increase data transmission safety.

In embodiments, the wearable device 102 and/or one or more of the devices 106, 108 may provide one or more of the following functions with respect to a subject: sensing, data storage, data analysis, presentation, and/or therapy. For example, in embodiments, the wearable device 102 and/or one or more of the devices 106, 108 may be used to measure any number of a variety of physiological, device, subjective, and/or environmental parameters associated with the subject 104, using electrical, mechanical, optical, and/or chemical means. The wearable device 102 and/or one or more of the devices 106, 108 may be configured to automatically gather data, gather data upon request (e.g., input provided by the subject, a clinician, another device, and/or the like), gather data in response to an event, and/or any number of various combinations and/or modifications thereof. The wearable device 102 and/or one or more of the devices 106, 108 may be configured to store data related to the physiological, device, environmental, and/or subjective parameters and/or transmit the data to any number of other devices in the system 100. The environmental parameters may include particulates, ultraviolet light, volatile organic compounds, and/or the like in the environment. The physiological parameters may include respiratory parameters (e.g., rate, depth, rhythm), motion parameters, (e.g., walking, running, falling, gait, gait rhythm), facial expressions, swelling, heart sounds, sweat, sweat composition (e.g., ammonia, pH, potassium, sodium, chloride), exhaled air composition, Electrocardiography (ECG) parameters, electroencephalogram (EEG) parameters, Electromyography (EMG) parameters, and/or the like. In embodiments, the wearable device 102 may include processing devices configured to process the sensed parameters, memory to store the sensed parameters, transmitters to transmit the sensed parameters, and/or receivers to receive one or more transmissions.

In embodiments, the wearable device 102 and/or one or more of the devices 106, 108 may be configured to analyze data and/or act upon the analyzed data. For example, the wearable device 102 and/or one or more of the devices 106, 108 may be configured to modify therapy, perform additional monitoring, store pre-analyzed or post-analyzed data, and/or provide alarm indications based on the analysis of the data.

In embodiments, the wearable device 102 and/or one or more of the devices 106, 108 may be configured to provide therapy. Therapy may be provided autonomously and/or upon request (e.g., an input by the subject 104, a clinician, another device or process, and/or the like). The wearable device 102 and/or one or more of the devices 106, 108 may be programmable in that various characteristics of their sensing, therapy (e.g., duration and interval), and/or communication may be altered by communication between the wearable device 102 and the one or more of the devices 106, 108. For example, in embodiments, one or more of the devices 106, 108 may be configured to communicate with the wearable device 102 to trigger the wearable device 102 to perform an action (e.g., a sensing action, a therapy action, etc.). In this manner, for example, timing of various activities performed by the wearable device 102 may be configured and maintained based on a communication scheme involving a number of the devices of the system 100.

According to embodiments, the wearable device 102 may include any number of different types of devices configured to be placed on, coupled to, embedded in, and/or otherwise interfaced with a subject's body (e.g., skin). For example, the wearable device 102 may include a middle portion arranged between two stiffer and/or thicker, end portions (illustrated in FIGS. 3-4). As another example, the wearable device 102 may include a portion enclosed and/or surrounded by a stiffer and/or thicker portion (e.g., a ring). As even another example, the wearable device 102 may include a portion partially enclosed and/or partially surrounded by a stiffer and/or thicker portion (e.g., a semi-circle). As even another example, the wearable device 102 may include a stiffer and/or thicker tubular section with thinner and/or more flexible portions arranged on the ends of the tubular sections. As even another example, the wearable device 102 may include thicker and/or stiffer extensions (e.g., spirals, elongate membranes, and/or the like) and thinner and/or more flexible substrate arranged between the extensions. While the embodiments disclosed herein are discussed in relation to the wearable device 102 including a middle portion arranged between two stiffer and/or thicker end portions, the embodiments contemplated include any of the examples set forth above wherein the wearable device 102 includes a thicker and/or stiffer section and a more flexible and/or thinner portion arranged and connected to the thicker and/or stiffer section.

In embodiments, one or more sensors 112 may be arranged on the middle portion allowing intimate contact with the subject and facilitating measuring physiological parameters of the subject while heavier electronic components may be arranged on the thicker, end portions, thereby facilitating a more durable construction of the wearable device. In embodiments, the thicker, end portions may be connected by a bridge portion (illustrated in FIGS. 3-4), thereby increasing the durability of the wearable device 102. In embodiments, the wearable device 102 may include an adhesive layer that facilitates the wearable device 102 being attached to the subject 104. Additionally or alternatively, the wearable device 102 may be attached to the subject 104 using another adhesive and/or compound not included in the wearable device 102. Additionally or alternatively, the wearable device 102 may be stamped and/or printed on the subject 104.

In embodiments, at least the middle portion of the wearable device 102 may be deformable so that the wearable device 102 is able to form to different contours of a subject 104 and/or flex and/or stretch, thereby accommodating movement of the subject 104. Due to the wearable device 102 deformation ability, the wearable device 102 may be able to be placed on different areas of the subject 104. For example, the wearable device 102 may be placed on one or more of the following areas of the subject 104: abdomen, chest, back, wrist, thigh, calve, foot, ankles, arm, hands, eyelids, ears, earlobes, penis, forehead, neck, and/or the like. These placements may facilitate sensing one or more environmental and/or physiological parameters set forth above Additionally or alternatively, the wearable device 102 may allow gases and/or liquids to permeate all or certain portions of the wearable device 102. The gas and/or liquid flow may be bidirectional or unidirectional. The wearable device 102 may allow some gases and/or liquids to permeate the wearable device 102 while preventing flow of other gases and/or liquids.

While one wearable device 102 is depicted in FIG. 1, in embodiments, there may be multiple wearable devices 102 positioned adjacent the body of a subject 104 and/or disposed on the body of the subject 104. In embodiments, each wearable device 102 may be configured to perform the same function as the other wearable devices 102 or perform different functions from the same or different locations. For example, a wearable device 102 may be placed on the chest of the subject 104 to record thoracic sounds and a wearable device 102 may be placed on the eyelid of the subject 104 to record eye movements (e.g., eyelid movements) indicative of REM sleep. Additionally or alternatively, a series of wearable devices 102 may be placed (e.g., subsequently in time) on a subject 104 whereby information from a first wearable device 102 may be used to adjust and/or modify functionality of an additional wearable device 102 such as, for example, an additional tattoo that was placed on the subject 104 at a later time than that of the first wearable device 102, that is configured to perform an action at a later time than the first wearable device 102, and/or the like.

According to embodiments, a number of wearable devices 102 may be configured to perform one or more functions in a cooperative manner, the cooperation of which may be managed by one or more of the wearable devices 102, the device 106 and/or the device 108. That is, for example, one or more wearable devices may be configured to transmit a signal (e.g., an acoustic signal, an electric signal, an optical signal, etc.), and one or more other wearable devices 102 may be configured to receive the transmitted signal and evaluate the attenuation or other characteristic of the signal to determine a characteristic about the media through which the signal traveled (e.g., to identify edema, measure transthoracic impedance, perform pulse oximetry, etc.). In embodiments, one or more wearable devices may be configured to cooperatively sense physiological parameters, provide coordinated therapy, and/or the like.

According to embodiments, the device 106 may be a wearable device (e.g., smartwatch), a portable computing device (e.g., smartphone), a medical device (e.g., a wearable medical device (WMD)), and/or the like. For example, the device 106 may include a control device, a monitoring device, a respiratory device, a pacemaker, a cardiac resynchronization therapy (CRT) device and/or the like, and may be a wearable device and/or medical device known in the art or later developed, for sensing physiological parameters of the subject 104, providing therapy and/or diagnostic data about the subject 104 and/or the device 106. In various embodiments, the device 106 may include inhaler functionality, nebulizer functionality, ventilating functionality, defibrillation, and pacing/CRT capabilities (e.g., a CRT-D device). In embodiments, the device 106 may be wearable on the subject 104 and may be configured to monitor (e.g., sense and/or record) physiological parameters associated with subject 104 (e.g., respiratory system, and/or circulatory system). In embodiments, the device 106 may be configured to record physiological parameters such as, for example, one or more respiratory signals, cardiac electrical signals, spirometry, oximetry, arterial blood gas measurements, heart sounds, heart rate, blood pressure measurements, oxygen saturations, and/or the like.

Additionally or alternatively, the device 106 may or may not be positioned adjacent the body of a subject 104 and/or disposed on the body of the subject 104. In embodiments, the device 106 may store data (e.g., medical data) and/or provide data to the wearable device 102 and/or the device 108 via a communication link 110. The data provided by the device 106 to one or more of the devices 102, 108 may facilitate one or more of the devices 102, 108 functioning as described above and below.

According to embodiments, the devices 106, 108 may include any type of medical device (e.g., an implantable medical device (IMD), etc.) that senses one or more physiological parameters of the subject 104, administers one or more therapies, and/or the like, and may include any number of different components of a medical device. For example, the device 108 may include a control device, a monitoring device, a respiratory device, a pacemaker, an implantable cardioverter defibrillator (ICD), a cardiac resynchronization therapy (CRT) device, a neurostimulation device, a drug delivery device, a muscular stimulation device, an optimal or audio stimulation device, and/or the like, and may be a medical device known in the art or later developed, for sensing physiological parameters, providing therapy and/or diagnostic data about the subject 104 and/or the device 108. In various embodiments, the device 108 may include a drug delivery functionality (e.g., an inhaler functionality, a nebulizer functionality and/or the like), ventilating functionality, defibrillation, an air filtration functionality, a smoking cessation functionality, an oxygen delivery functionality, a volatile compound release functionality, and/or pacing/CRT capabilities (e.g., a CRT-D device). In embodiments, the device 108 may be implanted subcutaneously within an implantation location or pocket in the patient's chest or abdomen and may be configured to monitor (e.g., sense and/or record) physiological parameters associated with one or more body systems of the subject 104 (e.g., the respiratory system, the nervous system, and/or the circulatory system). In embodiments, the device 108 may be an implantable respiratory monitor, an implantable cardiac monitor (ICM) (e.g., an implantable diagnostic monitor (IDM), an implantable loop recorder (ILR), etc.) configured to record physiological parameters such as, for example, one or more respiratory signals, cardiac electrical signals, spirometry, oximetry, arterial blood gas measurements, heart sounds, heart rate, blood pressure measurements, oxygen saturations, and/or the like.

In addition, the wearable device 102 may include one or more sensors 112 configured to detect a variety of physiological parameters and/or environmental parameters that may be used in connection with various diagnostic, therapeutic and/or monitoring implementations. For example, the wearable device 102 may include sensors 112 or circuitry for detecting respiratory system signals, cardiac system signals, heart sounds, and/or signals related to subject's 104 activity. In embodiments, the wearable device 102 may be configured to sense intrathoracic impedance, from which various respiratory parameters may be derived, including, for example, respiratory tidal volume and minute ventilation. Sensors 112 and associated circuitry may be incorporated in connection with the wearable device 102 for detecting one or more body movement or body posture and/or position related signals. For example, accelerometers, gyroscopes, and/or GPS devices may be employed to detect patient activity, patient location, body orientation, and/or torso position.

Derived parameters may also be monitored using the wearable device 102. For example, a respiration sensor 112 may rely on measurements taken by an implanted accelerometer that measures body activity levels, respiration sounds, chest movement with respiration, heart sounds, and/or the like. The respiration sensor 112 may include one or more electrodes configured to sense a physiological electrical signal, from which a respiration signal may be extracted. Respiration signals may additionally, or alternatively, be extracted from heart sound signals, cardiac electrical signals (e.g., electrograms), and/or the like. The respiration sensor 112 may be used to estimate respiration patterns based on the measured parameters.

Respiration sensors can be used to determine tidal volume (VT), respiration rate, peak expiratory flow rate (PEFR), forced expiratory volume (FEV), and a composite respiration index that includes at least one of an inspiration/expiration ratio (IER), VT times respiration rate, and respiration rate divided by VT. Respiration sensors may include any number of different types of sensors, including thoracic impedance sensors, accelerometers, flow sensors, and electrocardiograms (ECG or EKG). For example, the respiration rate can be sensed by one or more of a thoracic impedance sensor, an accelerometer, and an ECG. Also, the PEFR and the FEV can be determined using a thoracic impedance sensor to measure VT, and the IER can be determined using a thoracic impedance to measure VT. Other parameters associated with a respiratory functional test can also be used in determining asthma status. These parameters include the VT, FEV, and PEFR parameters, minute volume (MV), vital capacity (VC), functional residual capacity (FRC), total lung capacity, forced vital capacity (FVC), and forced expiratory flow (FEF).

Sound sensors can include at least one of a lung sound sensor, a speech sensor, and a heart sound sensor, where the lung sound sensor can be configured to sense wheezing in the patient. In embodiments, sound sensors include one or more of an accelerometer, a hydrophone, and a microphone. For example, a speech sensor and a lung sound sensor for sensing wheezing can include one or more of an accelerometer and a microphone.

In embodiments, a heart rate sensor includes an ECG for measuring the heart rate, an oxygen sensor includes an optical oxygen saturation sensor, and a central cyanosis sensor includes an optical oxygen saturation sensor. Also, in embodiments, a muscle use sensor and an activity sensor include one or more of a cervical and thoracic impedance sensor and an electromyogram for measuring activity. In addition, a posture sensor and an altered consciousness sensor include an accelerometer for measuring posture and/or balance. The inflammation sensor includes a chemical sensor for detecting an inflammatory marker, such as nitric oxide, and the sleep quality sensor includes one or more of a thoracic impedance sensor, an accelerometer, and an ECG for measuring tidal volume, respiration rate activity, posture, and heart rate. In embodiments, a sleep monitoring sensor may include an accelerometer that is incorporated into the e-tattoo 106 that is positioned on the eyelid of the subject 104.

In embodiments, a chemical sensor includes one or more of an inflammatory marker, e.g., a C-reactive protein, a pharmaceutical agent, e.g., theophylline, beta blockers, and/or aspirin, a blood gas, e.g., oxygen and/or carbon dioxide, and blood cell count, e.g., an eosinophil count. In embodiments, for example, a breath sensor include a chemical sensor such as, for example, a nitric oxide test, where increased levels of exhaled nitric oxide indicate inflammation, which can, for example, indicate a worsening asthma status.

Additionally or alternatively, the sensor 112 may be configured to sense other physiological information about the subject 104 and/or environmental information. The physiological information may include at least one of: a respiration sensor, a sound sensor, a heart rate sensor, an oxygen sensor, a muscle use sensor, an activity sensor, a posture sensor, an inflammation sensor, a chemical sensor, an exhaled breath sensor, a thoracic composition sensor, an altered consciousness sensor, a central cyanosis sensor, and a sleep quality sensor. The environmental information may include but is not limited to information about the external environment (e.g., temperature, air quality, humidity, carbon monoxide level, oxygen level, barometric pressure, light intensity, sound, and/or the like) to which the subject 104 is exposed, and/or the like. Additionally or alternatively, the wearable device 102 may be configured to sense parameters, via the sensor 112 relating to the human body, such as temperature (e.g., a thermometer), blood pressure (e.g., a sphygmomanometer), blood characteristics (e.g., glucose levels), body weight, physical strength, mental acuity, diet, heart characteristics, relative geographic position (e.g., a Global Positioning System (GPS)), and/or the like.

The illustrative system 100 shown in FIG. 1 is not intended to suggest any limitation as to the scope of use or functionality of embodiments of the present disclosure. The illustrative system 100 should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the subject matter disclosed herein.

Various components depicted in FIG. 1 may operate together to form the system 100, which may be, for example, a computerized patient management and monitoring system. In embodiments, the system 100 may be designed to assist in monitoring the subject's condition, managing the subject's therapy, and/or the like. An illustrative patient management and monitoring system is the LATITUDE® patient management system from Boston Scientific Corporation, Marlborough Mass. Illustrative aspects of a patient management and monitoring system are described in ADVANCED PATIENT MANAGEMENT SYSTEM INCLUDING INTERROGATOR/TRANSCEIVER UNIT, U.S. Pat. No. 6,978,182 to Mazar et al., the entirety of which is hereby incorporated by reference herein.

Figure 2:
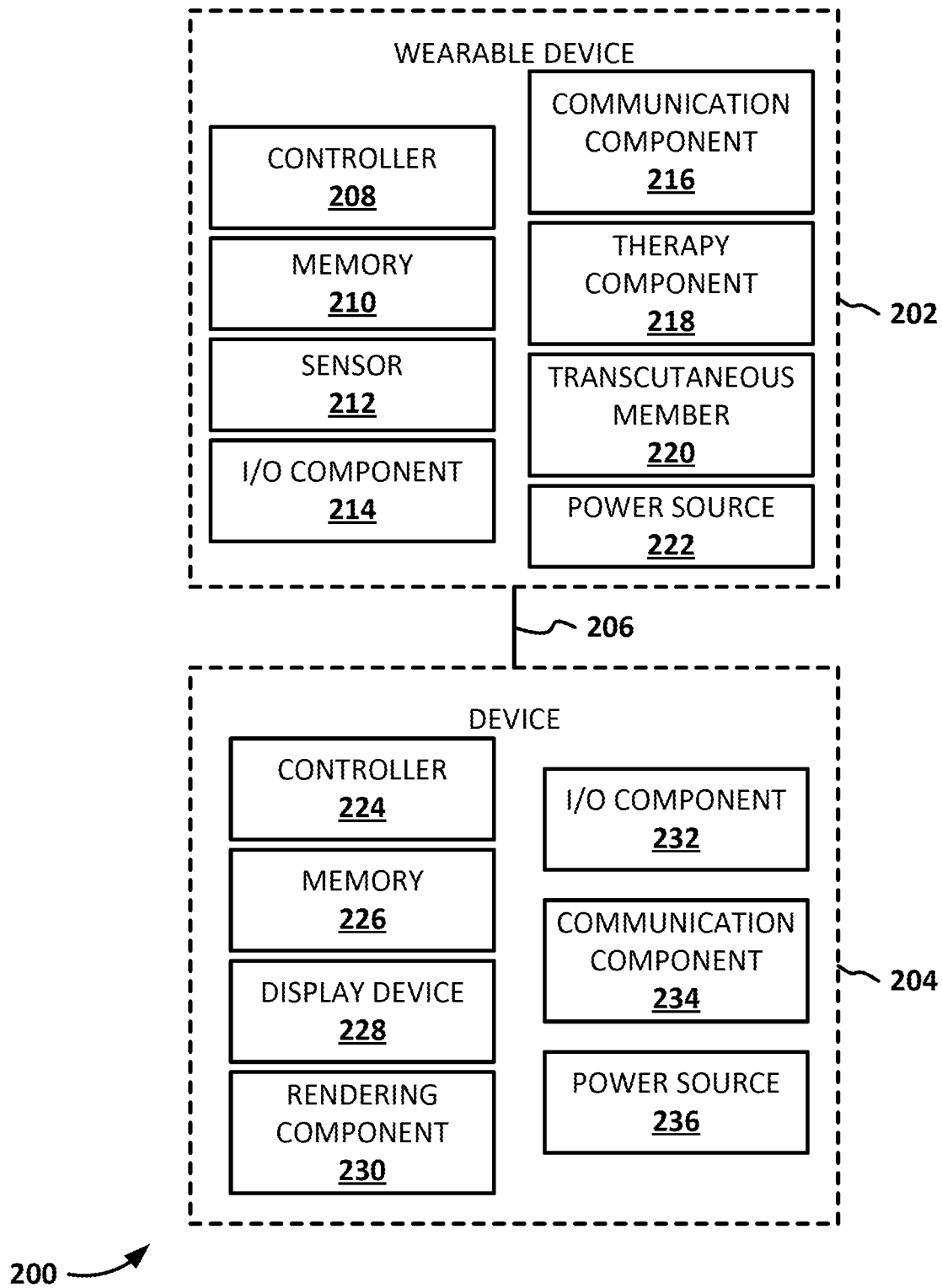
FIG. 2 is a block diagram depicting an illustrative operating environment, in accordance with embodiments of the subject matter disclosed herein.

FIG. 2 is a block diagram depicting an illustrative operating environment 200, in accordance with embodiments of the subject matter disclosed herein. According to embodiments, the operating environment 200 may be, be similar to, include, be included in, or correspond to the system 100 depicted in FIG. 1. As shown in FIG. 2, the illustrative operating environment 200 includes a wearable device 202 configured to communicate with a device 204 via a communication link 206. In embodiments, the operating environment 200 may include the wearable device 202 without including the device 204.

According to embodiments, the wearable device 202 may be, be similar to, include, or be included in the wearable device 102 depicted in FIG. 1. The device 204 may be, be similar to, include, or be included in the device 106 and/or the device 108 depicted in FIG. 1. And, similarly, the communication link 206 may be, be similar to, include, or be included in the communication link 110 depicted in FIG. 1. According to embodiments, the operating environment 200 may include any number of other devices and/or any other types of devices, for example, additional medical devices, mobile devices, additional wearable devices, and/or the like.

According to embodiments illustrated in FIG. 2, the wearable device 202 includes a controller 208, a memory 210, a sensor 212, an input/output (I/O) component 214, a communication component 216, a therapy component 218, a transcutaneous member 220, and/or a power source 222.

The controller 208 may include, for example, a processing unit, a pulse generator, and/or the like. The controller 208 may be any arrangement of electronic circuits, electronic components, processors, program components and/or the like configured to store and/or execute programming instructions, to direct the operation of the other functional components of the wearable device 202, to instruct the sensor 212 to sense one or more physiological parameters of a subject (e.g., the subject 104), to instruct the sensor 212 to sense one or more environmental parameters, to store physiologic data obtained by the sensor 212, to instruct the therapy component 218 to provide one or more therapies, and/or the like, and may be implemented, for example, in the form of any combination of hardware, software, and/or firmware.

In embodiments, the controller 208 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the controller 208 may include a processing unit configured to communicate with memory to execute computer-executable instructions stored in the memory. Although the controller 208 is referred to herein in the singular, the controller 208 may be implemented in multiple instances, distributed across multiple computing devices, instantiated within multiple virtual machines, and/or the like.

The controller 208 may also be configured to store information in the memory 210 and/or access information from the memory 210. The controller 208 may execute instructions and perform desired tasks as specified by computer-executable instructions stored in the memory 210.

In embodiments, the memory 210 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

The wearable device 202 may sense various physiological and/or environmental parameters using a sensor 212. The environmental parameters may include particulates, ultra-violet light, volatile organic compounds, and/or the like in the environment. The physiological parameters may include respiratory parameters (e.g., rate, depth, rhythm), motion parameters, (e.g., walking, running, falling, gait, gait rhythm), facial expressions, swelling, heart sounds, sweat, sweat composition (e.g., ammonia, pH, potassium, sodium, chloride), exhaled air composition, cardiac parameters, Electrocardiography (ECG) parameters, electroencephalogram (EEG) parameters, Electromyography (EMG) parameters, and/or the like. To sense the one or more environmental parameters and/or physiological parameters, the sensor 212 may include temperature sensors (e.g., thermocouples or thermistors), barometers, acoustic sensors, pressure sensors, optical sensors, motion or impact sensors (e.g., accelerometers, gyroscopes, inertial measuring units (IMUs)), strain sensors, Doppler systems, chemical sensors, ultrasound sensors, and/or the like, in any number of various types of configurations.

The I/O component 214 may include and/or be coupled to a user interface configured to present information to a user or receive indication from a user. For example, the I/O component 214 may include and/or be coupled to a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, a volatile compound release depot, and/or the like. In embodiments, the I/O component 214 may be used to present and/or provide an indication of any of the data sensed and/or produced by the wearable device 202. According to embodiments, for example, the I/O component 214 may include one or more visual indicators (e.g., single-color LED lights, multi-color LED lights, a flexible digital display device, and/or the like) configured to provide information to a user (e.g., by illuminating, flashing, displaying data, etc.). Additionally or alternatively, the I/O component 214 may be used to control therapy provided by the wearable device 202.

The communication component 216 may be configured to communicate (i.e., send and/or receive signals) with the device 204 and/or any other device. Additionally or alternatively, any data sensed by the sensor 212 may be transmitted to the device 204 for processing and/or storage.

In embodiments, the communication component 216 may include, for example, circuits, program components, and one or more transmitters and/or receivers for communicating wirelessly with one or more other devices such as, for example, the device 204. According to various embodiments, the communication component 216 may include one or more transmitters, receivers, transceivers, transducers, and/or the like, and may be configured to facilitate any number of different types of wireless communication such as, for example, radio-frequency (RF) communication, microwave communication, infrared or visual spectrum communication, acoustic communication, inductive communication, conductive communication, and/or the like. The communication component 216 may include any combination of hardware, software, and/or firmware configured to facilitate establishing, maintaining, and using any number of communication links.

The therapy component 218 may be configured to delivery therapy in response to one or more sensed and/or derived signals. In embodiments, the therapy component 218 may include any number of different therapy components such as, for example, an inhaler component, a nebulizer component, a drug delivery component, defibrillation component, a neurostimulation component, a neuromodulation component, a temperature regulation component, and/or the like.

In embodiments, the wearable device 202 may have a transcutaneous member 220 piercing the skin of subject (e.g., subject 104). The transcutaneous member 220 may contain one or more sensors measuring parameters within a subject (i.e. a blood parameter, an interstitial fluid parameter, an electrical parameter). The transcutaneous member 220 may contain one or more components (e.g. an electrode, a catheter) for delivering one or more therapies (e.g. a neurostimulation therapy, a drug therapy). In an embodiment, the transcutaneous member 220 may measure glucose and/or deliver insulin.

The power source 222 provides electrical power to the other operative components (e.g., the controller 208, the memory 210, the sensor 212, the I/O component 214, the communication component 216, and the therapy component 218), and may be any type of power source suitable for providing the desired performance and/or longevity requirements of the wearable device 202. In various embodiments, the power source 222 may include one or more batteries, which may be rechargeable (e.g., using an external energy source). The power source 222 may include one or more capacitors, energy conversion mechanisms, and/or the like. Additionally or alternatively, the power source 222 may harvest energy from a subject (e.g., the subject 104) (e.g. motion, heat, biochemical) and/or from the environment (e.g. electromagnetic). Additionally or alternatively, the power source 222 may harvest energy from an energy source connected to the body, for example, a shoe may receive energy from impact and send the received energy to a power source 222 of the wearable device 202.

As shown in FIG. 2, the device 204 includes a controller 224, a memory 226, a display device 228, a rendering component 230, an I/O component, 232 a communication component 234, and a power source 236. The controller 224 may include, for example, a processing unit, a pulse generator, and/or the like. The controller 224 may be any arrangement of electronic circuits, electronic components, processors, program components and/or the like configured to store and/or execute programming instructions, to direct the operation of the other functional components of the device 204, to store physiologic data obtained by the wearable device 202, and/or the like, and may be implemented, for example, in the form of any combination of hardware, software, and/or firmware.

In embodiments, the controller 224 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the controller 224 may include a processing unit configured to communicate with memory to execute computer-executable instructions stored in the memory. Although the controller 224 is referred to herein in the singular, the controller 224 may be implemented in multiple instances, distributed across multiple computing devices, instantiated within multiple virtual machines, and/or the like.

The controller 224 may also be configured to store information in the memory 226 and/or access information from the memory 226. The controller 224 may execute instructions and perform desired tasks as specified by computer-executable instructions stored in the memory 226. In embodiments, for example, the controller 224 may be configured to instantiate, by executing instructions stored in the memory 226.

In embodiments, the memory 226 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

The display device 228 can include, but is not limited to, one of the following display devices: a cathode ray tube (CRT) display, a light emitting diode (LED) display, or a liquid crystal display (LCD) display.

The rendering component 230 may be configured to receive, from the wearable device 202, sensed physiological parameters; and cause the display device 228 to present a representation of the physiological parameters. According to embodiments, the rendering component 230 may be configured to interpret, analyze, and/or otherwise process physiological parameters prior to presenting representations thereof. In embodiments, the rendering component 230 may provide, via a GUI, interactive representations of physiological parameters. Representations of physiological parameters may include, for example, parameter values, indications of diagnoses, graphs, charts, anatomical maps, images (e.g., ultrasound images), and/or the like. According to embodiments, the rendering component 230 may also be configured to receive, via a GUI, inputs from a user that indicate parameter settings for a particular sensing task. That is, for example, the GUI may facilitate user control of any number of aspects of operation of the device 204.

The I/O component 232 in conjunction with the rendering component 230 may include and/or be coupled to a user interface configured to present information to a user or receive indication from a user. For example, the I/O component 232 may include and/or be coupled to the display device 228, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, a volatile compound release depot, and/or the like. In embodiments, the I/O component 232 may be used to present and/or provide an indication of any of the data sensed and/or produced by the wearable device 202 and/or the device 204. According to embodiments, for example, the I/O component 232 may include one or more visual indicators (e.g., single-color LED lights, multi-color LED lights, a flexible digital display device, and/or the like) configured to provide information to a user (e.g., by illuminating, flashing, displaying data, etc.).

The communication component 234 may be configured to communicate (i.e., send and/or receive signals) with the wearable device 202 and/or any other device. Additionally or alternatively, any data sensed by the sensor 212 may be transmitted to the device 204 for processing and/or storage.

In embodiments, the communication component 234 may include, for example, circuits, program components, and one or more transmitters and/or receivers for communicating wirelessly with one or more other devices such as, for example, the wearable device 202. According to various embodiments, the communication component 234 may include one or more transmitters, receivers, transceivers, transducers, and/or the like, and may be configured to facilitate any number of different types of wireless communication such as, for example, radio-frequency (RF) communication, microwave communication, infrared or visual spectrum communication, acoustic communication, inductive communication, conductive communication, and/or the like. The communication component 234 may include any combination of hardware, software, and/or firmware configured to facilitate establishing, maintaining, and using any number of communication links.

The power source 236 provides electrical power to the other operative components (e.g., the controller 224, the memory 226, the display device 228, the rendering component 230, the I/O component 232, and the communication component 234), and may be any type of power source suitable for providing the desired performance and/or longevity requirements of the device 204. In various embodiments, the power source 204 may include one or more batteries, which may be rechargeable (e.g., using an external energy source). The power source 204 may include one or more capacitors, energy conversion mechanisms, and/or the like. In embodiments, the power source 236 may transfer power to the power source 222 using a wireless or non-wireless connection (e.g., via conduction, induction, radio-frequency, etc.). Because the wearable device 202 may be a small device, as explained in more detail below, the power source 222 may not be capable of storing a lot of power and, therefore, the longevity of the wearable device 202 may be increased via power transfer from the device 204 to the wearable device 202.

The illustrative operating environment 200 shown in FIG. 2 is not intended to suggest any limitation as to the scope of use or functionality of embodiments of the present disclosure. The illustrative operating environment 200 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

FIGS. 3A-3B are schematic illustrations of a wearable device 300, in accordance with embodiments of the disclosure. In particular, FIG. 3A is a top view of the wearable device 300 and FIG. 3B is a side sectional view of the wearable device 300.

In embodiments, the wearable device 300 may include a middle portion 302 arranged between two end portions 304. Each of the middle portion 302 and end portions 304 may be formed from one or more substrates and one or more layers of one or more substrates. For example, the middle portion 302 and the end portions 304 may be formed from the same substrate(s) and/or different substrates. Exemplary substrate materials include, but are not limited to: metal film, silicon, graphene, Polyethylene terephthalate (PET), polyimide (PI), Polyethylene naphthalate (PEN), polyetherimide (PEI), fluropolymers (FEP), cellulose, copolymers and/or the like. Additionally or alternatively, the end portions 304 may be injection molded from, for example, thermoplastic polyurethane (TPU), nylon, and/or the like.

In embodiments, the end portions 304 may be the same width 306A, 306B and/or have different widths 306A, 306B. Additionally or alternatively, the end portions 304 may have the same thicknesses 308A, 308B and/or different thicknesses 308A, 308B.

In embodiments, the middle portion 302 may be more flexible than the end portions 304. The middle portion 302 may be more flexible than the end portions 304 due to being thinner than the end portions 304, i.e., the middle portion 302 having a thickness 308C that is less than the thicknesses 308A, 308B. For example, the middle portion 302 may have a thickness 308C that is approximately equal to or less than 10 micrometers and the end portions 304 may have a thickness 308A, 308C that is approximately equal to or greater than 10 micrometers. Additionally or alternatively, the middle portion 302 may be more flexible than the end portions 304 due to being comprised of a more flexible material than the end portions 304. Additionally or alternatively, the middle portion 302 may be more stretchable than the end portions 304.

In embodiments, the middle portion 302 and end portions 304 may each have a proximal side 310A-310C and a distal side 312A-312C that is opposite the proximal side 310A-310C. In embodiments, one or more of the proximal sides 310A-310C may be configured to be attached to a subject 314. For example, one or both of the proximal sides 310A-310B of the end portions 304 may be configured to be attached to a subject 314. To attach to the subject 314, one or both of the proximal sides 310A-310B of the end portions 304 may include an adhesive 316 configured to adhere to the subject 314. For example, the adhesive 316 may be silicon-based adhesives, e.g. Silpuran® 2130 and/or Silbione 4717, and/or and/or acrylic-based adhesives. Additionally or alternatively, one or more antibiotic materials may be incorporated into the adhesive 316 to, for example, extend the use of the wearable device 300. For example, one or more antibiotic materials may be incorporated into the adhesives 316: metal salts and/or metal ions (e.g. copper, silver), antibiotics (e.g., neomycin, soframycin, bacitracin, polymycin), antibacterials, (e.g., chlorhexidine), its salts (e.g., quaternary ammonium compounds—cetrimide, domiphen bromide, polymeric quaternaries) and/or iodophors (e.g., povidone iodine).

Additionally or alternatively, the adhesive 316 may be applied one or more of the proximal sides 310A-310B and/or the subject 314 in order to adhere the wearable device 300 to the subject 314. Additionally or alternatively, the proximal side 310C of the middle portion 302 may also include an adhesive (not shown) and/or an adhesive may be applied to the proximal side 310C to facilitate attachment of the wearable device 300 to the subject 314.

As illustrated, one or more electronic components 318A, 318B may be arranged on one or more of the portions 302, 304. An exemplary electronic component 318A may be one or more sensors (e.g., sensor 212) configured to sense one or more physiological parameters of the subject 314 and/or environmental parameters using electrical, mechanical, optical, and/or chemical means. In embodiments, the sensor 318A may be arranged on the middle portion 302. Due to the increased flexibility and/or stretchiness of the middle portion 302 in comparison to the end portions 304, the middle portion 302 may better conform to the contours of the subject 314 and/or be in better contact with the subject 314. As such, more accurate physiological measurements of the subject 314 may be obtained by the wearable device 300. Exemplary physiological parameters may include, but are not limited to: respiratory parameters (e.g., rate, depth, rhythm), motion parameters, (e.g., walking, running, falling, gait, gait rhythm), facial expressions, swelling, heart sounds, sweat, sweat composition (e.g., ammonia, pH, potassium, sodium, chloride), exhaled air composition, Electrocardiography (ECG) parameters, electroencephalogram (EEG) parameters, Electromyography (EMG) parameters, and/or the like. Exemplary environmental parameters may include, but are not limited to: particulates, ultraviolet light, volatile organic compounds, and/or the like in the environment.

As illustrated, one or more electronic components 318B may be arranged on the end portions 304. Exemplary electronic components 318B include, but are not limited to controllers (e.g., controller 208), memory (e.g., memory 210), I/O components (e.g., I/O components 214), communication components (e.g., communication components 216), therapy components (e.g., therapy components 218), transcutaneous members (e.g., transcutaneous members 220), and/or power sources (e.g., power sources 222). In embodiments, the electronic components 318B may include processing devices configured to process the sensed parameters of the electronic component 318A, memory to store the sensed parameters, transmitters to transmit the sensed parameters, and/or receivers to receive one or more transmissions.

In embodiments, due to the reduced flexibility of the end portions 304 in comparison to the middle portion 302, the end portions 304 may be better suited to have one or more types of electronic components 3188 arranged thereon. For example, it may be less likely the wearable device 300 is damaged by arranging a battery and/or a controller that has high temperature variability and/or may be heavier than other types of electronic components on the end portions 304 than on the middle portion 302.

In embodiments, the wearable device 300 may include one or more bridge portions 320. The bridge portion 320 may have a thickness 308D that is greater than the thickness of the middle portion 302 and/or be comprised of a material that is more rigid than the material of the middle portion 302. As such, the bridge portion 320 may increase the structural integrity of the wearable device 300 by providing a bridge between and/or connect the end portions 304. To connect the end portions 304, the bridge portions 320 may extend along the sides 322 of the middle portion 302. Additionally or alternatively, the bridge portion 320 may be formed from the same substrate(s) as the end portions 304 or different substrates.

FIGS. 4A-4B are schematic illustrations of a wearable device 400, in accordance with embodiments of the disclosure. In particular, FIG. 4A is a top view of the wearable device 400 and FIG. 4B is a side sectional view of the wearable device 400.

In embodiments, the wearable device 400 may have some of the same characteristics as the wearable device 400. For example, the wearable device 400 may include a middle portion 402 arranged between two end portions 404. Each of the middle portion 402 and end portions 404 may be formed from one or more substrates and one or more layers of one or more substrates. For example, the middle portion 402 and the end portions 404 may be formed from the same substrate(s) or different substrates. Exemplary substrate materials include, but are not limited to: metal film, silicon, graphene, Polyethylene terephthalate (PET), polyimide (PI), Polyethylene naphthalate (PEN), polyetherimide (PEI), fluropolymers (FEP), cellulose, copolymers and/or the like. Additionally or alternatively, the end portions 404 may be injection molded from, for example, thermoplastic polyurethane (TPU), nylon, and/or the like. In embodiments, the end portions 404 may be the same width 406A, 406B and/or have different widths 406A, 406B. Additionally or alternatively, the end portions 404 may have the same thicknesses 408A, 408B and/or different thicknesses 408A, 408B.

In embodiments, the middle portion 402 may be more flexible than the end portions 404. The middle portion 402 may be more flexible than the end portions 404 due to being thinner than the end portions 404, i.e., the middle portion 402 having a thickness 408C that is less than the thicknesses 408A, 408B. For example, the middle portion 402 may have a thickness 408C that is approximately equal to or less than 10 micrometers and the end portions 404 may have a thickness 408A, 408C that is approximately equal to or greater than 10 micrometers. Additionally or alternatively, the middle portion 402 may be more flexible than the end portions 404 due to being comprised of a more flexible material than the end portions 404. Additionally or alternatively, the middle portion 402 may be more stretchable than the end portions 404.

In embodiments, the middle portion 402 and end portions 404 may each have a proximal side 410A-410C and a distal side 412A-412C that is opposite the proximal side 410A-410C. In embodiments, one or more of the proximal sides 410A-410C may be configured to be attached to a subject 414. For example, one or both of the proximal sides 410A, 410B of the end portions 404 may be configured to be attached to a subject 414. To attach to the subject 414, one or both of the proximal sides 410A, 410B may include an adhesive 416 configured to adhere to the subject 414. For example, the adhesive 416 may be silicon-based adhesives, e.g. Silpuran® 2130 and/or Silbione 4717, and/or and/or acrylic-based adhesives. Additionally or alternatively, one or more antibiotic materials may be incorporated into the adhesive 416 to, for example, extend the use of the wearable device 400. For example, one or more antibiotic materials may be incorporated into the adhesives 416: metal salts and/or metal ions (e.g. copper, silver), antibiotics (e.g., neomycin, soframycin, bacitracin, polymycin), antibacterials, (e.g., chlorhexidine), its salts (e.g., quaternary ammonium compounds—cetrimide, domiphen bromide, polymeric quaternaries) and/or iodophors (e.g., povidone iodine).

Additionally or alternatively, the adhesive 416 may be applied one or more of the proximal sides 410A, 410B and/or the subject 404 in order to adhere the wearable device 400 to the subject 414. Additionally or alternatively, the proximal side 410C of the middle portion 402 may also include an adhesive (not shown) and/or an adhesive may be applied to the proximal side 410C to facilitate attachment of the wearable device 400 to the subject 414.

As illustrated, one or more electronic components 418A-418C may be arranged on one or more of the portions 402, 404. An exemplary electronic component 418A may be one or more sensors (e.g., sensor 212) configured to sense one or more physiological parameters of the subject 414 and/or environmental parameters using electrical, mechanical, optical, and/or chemical means. In embodiments, the sensor 418A may be arranged on the middle portion 402. Due to the increased flexibility and/or stretchiness of the middle portion 402 in comparison to the end portions 404, the middle portion 402 may better conform to the contours of the subject 414 and/or be in better contact with the subject 414. As such, more accurate physiological measurements of the subject 414 may be obtained by the wearable device 400. Exemplary physiological parameters may include, but are not limited to: respiratory parameters (e.g., rate, depth, rhythm), motion parameters, (e.g., walking, running, falling, gait, gait rhythm), facial expressions, swelling, heart sounds, sweat, sweat composition (e.g., ammonia, pH, potassium, sodium, chloride), exhaled air composition, Electrocardiography (ECG) parameters, electroencephalogram (EEG) parameters, Electromyography (EMG) parameters, and/or the like. Exemplary environmental parameters may include, but are not limited to: particulates, ultraviolet light, volatile organic compounds, and/or the like in the environment.

As illustrated, one or more electronic components 418B may be arranged on the end portions 404. Exemplary electronic components 418B include, but are not limited to controllers (e.g., controller 208), memory (e.g., memory 210), I/O components (e.g., I/O components 214), communication components (e.g., communication components 216), therapy components (e.g., therapy components 218), transcutaneous members (e.g., transcutaneous members 220), and/or power sources (e.g., power sources 222). In embodiments, the electronic components 418B may include processing devices configured to process the sensed parameters of the electronic component 418A, memory to store the sensed parameters, transmitters to transmit the sensed parameters, and/or receivers to receive one or more transmissions.

In embodiments, due to the reduced flexibility of the end portions 404 in comparison to the middle portion 402, the end portions 404 may be better suited to have one or more types of electronic components 4188 arranged thereon. For example, it may be less likely the wearable device 400 is damaged by arranging a battery and/or a controller that has high temperature variability and/or may be heavier than other types of electronic components on the end portions 404 than on the middle portion 402.

In embodiments, the wearable device 400 may include one or more bridge portions 420. The bridge portion 420 may be comprised of a material that is more rigid than the material of the middle portion 402. As such, the bridge portion 420 may increase the structural integrity of the wearable device 400 by providing a bridge between and/or connect the end portions 404. Additionally or alternatively, the bridge portion 420 may be opaque to one or more types of light to help protect the middle portion 402 and/or the one or more electronic components 418A arranged on the middle portion 402. For example, the bridge portion 420 may be opaque to visible light and/or ultraviolet light.

To connect the end portions 404, the bridge portions 420 may be distal to and spaced apart from the middle portion 402 (as shown in FIG. 4A) and extend from a side 422A of an end portion 402 to a side 422B of the other, end portion 402. In embodiments, the bridge portion 420 may extend the entire depth 424 of one or both of the end portions 404 (as illustrated) or may extend less than the entire depth 424 of one or both of the end portions 404. Additionally or alternatively, the bridge portion 420 may be formed from the same substrate(s) as the end portions 404 or different substrates.

In embodiments, an electronic component 418C may be arranged between the middle portion 402 and the bridge portion 420. An exemplary electronic component 418C arranged between the middle portion 402 and the bridge portion 420 may be a capacitor 418C. For example, the capacitor 418C may include a first conductive surface 426A arranged on a distal side 412C of the middle portion 402 and a second conductive surface 426B arranged on a proximal side 428A of the bridge portion 420 such that the first conductive surface 426A is electrically isolated from the second conductive surface 426B. In embodiments, respective electrical leads may be attached to the conductive surfaces 426A, 426B. In embodiments, a deformable dielectric 430 may be arranged between the first conductive surface 426A and the second conductive surface 426B. In embodiments, electrical signals sensed by the electrical leads connected to the conductive surfaces 426A, 426B may be used to determine a change in capacitance of the capacitor 418C and based on the elastic modulus of the dielectric 430, a pressure on the multilayer wearable device 400 may be determined.

Additionally or alternatively, an electronic component 418D may be arranged on a distal side 428B of the bridge portion 420. In embodiments, the electronic component 418D may be an optical component 418D. The optical components may determine a physiological parameter of the subject 314 by emitting light through the middle portion 304 and receiving reflected light from the subject 314 and/or emitting light onto the middle portion 304 and receiving reflected light from the middle portion 304. In embodiments, the wavelength of the emitted light from the optical component 418D may be approximately between 600 nanometers and 1000 nanometers. However, this is only an example and not meant to be limiting.

In embodiments, the middle portion 402 may be porous and include one or more pores 432 that penetrate the entire thickness of the middle portion 402. In embodiments, the pores 432 may be of a size that allows an active pharmaceutical ingredient 434 to pass through the middle portion 402 to the subject 414. Exemplary active pharmaceutical ingredients 434 include but are not limited to: anti-bacterial, anti-inflammatory compounds, anti-asthmatic compounds (e.g., Zileuton), active pharmaceutical ingredients used in epicutaneous immunotherapy, nitroglycerin, testosterone, nicotine, opiate (e.g. Fentanyl, Buprenorphine), antimuscarinic (e.g. Scopolamine, Oxybutynin), estrogen (e.g. Estradiol, Estradiol, Norethisterone Acetate), contraceptive (e.g. Norelgestromin & EthinylEstradiol), monoamine oxidase (MAO) inhibitors (e.g. Selegeline), dopamine agonists (e.g. Rotigotine), cholinesterase inhibitors (e.g. Rivastigmine), 5HT3 inhibitors (e.g. Granisetron), central nervous system stimulants (e.g. Methylphenidate), alpha-agonist hypotensive (e.g. Clonidine), and/or the like. Additionally or alternatively, the active pharmaceutical ingredient 434 may be triggered to release during specific parts of the day (e.g., only during sleep). As such, the wearable device 400 may be used to deliver an active pharmaceutical ingredient 434 to the subject 414 by disposing the active pharmaceutical ingredient 434 between the middle portion 402 and the bridge portion 420.

In embodiments electronic component 418C may be a chemical sensor capable of sensing analytes that permeate proximal side 410C via pores 432. For example, electronic component 418C may sense one or more chemical biomarkers such as an electrolyte (e.g. sodium, potassium), glucose, lactate, a toxin (e.g. arsenic, cadmium, lead, and mercury), or/and a therapeutic agent (e. g. antibiotic, diuretic).

In embodiments, a substance 436 may be arranged between the middle portion 402 and the bridge portion 420. In embodiments, the substance 436 may facilitate separation of the middle portion 402 and the bridge portion 420.

In embodiments, the substance 436 may be a gel 436. Exemplary gels 436 include, but are not limited to: AMPS (2-acrylamido-2-methylpropane sulfonic acid sodium salt), PEGDA (polyethylene glycol diacrylate), PVA (Polyvinyl alcohol), PVP (Polyvinyl pyrrolidone), PEG (polyethylene glycol), Chitosan, keratin, and/or the like. Additionally, the gel 436 may include one or more particles (e.g., microparticles) (not shown). In embodiments, the particles may assist the gel 436 in maintaining separation between the middle portion 402 and the bridge portion 420. Exemplary particles include but are not limited to Poly(methyl methacrylate) (PMMA), silica, and/or hollow glass microbeads.

Figure 5:
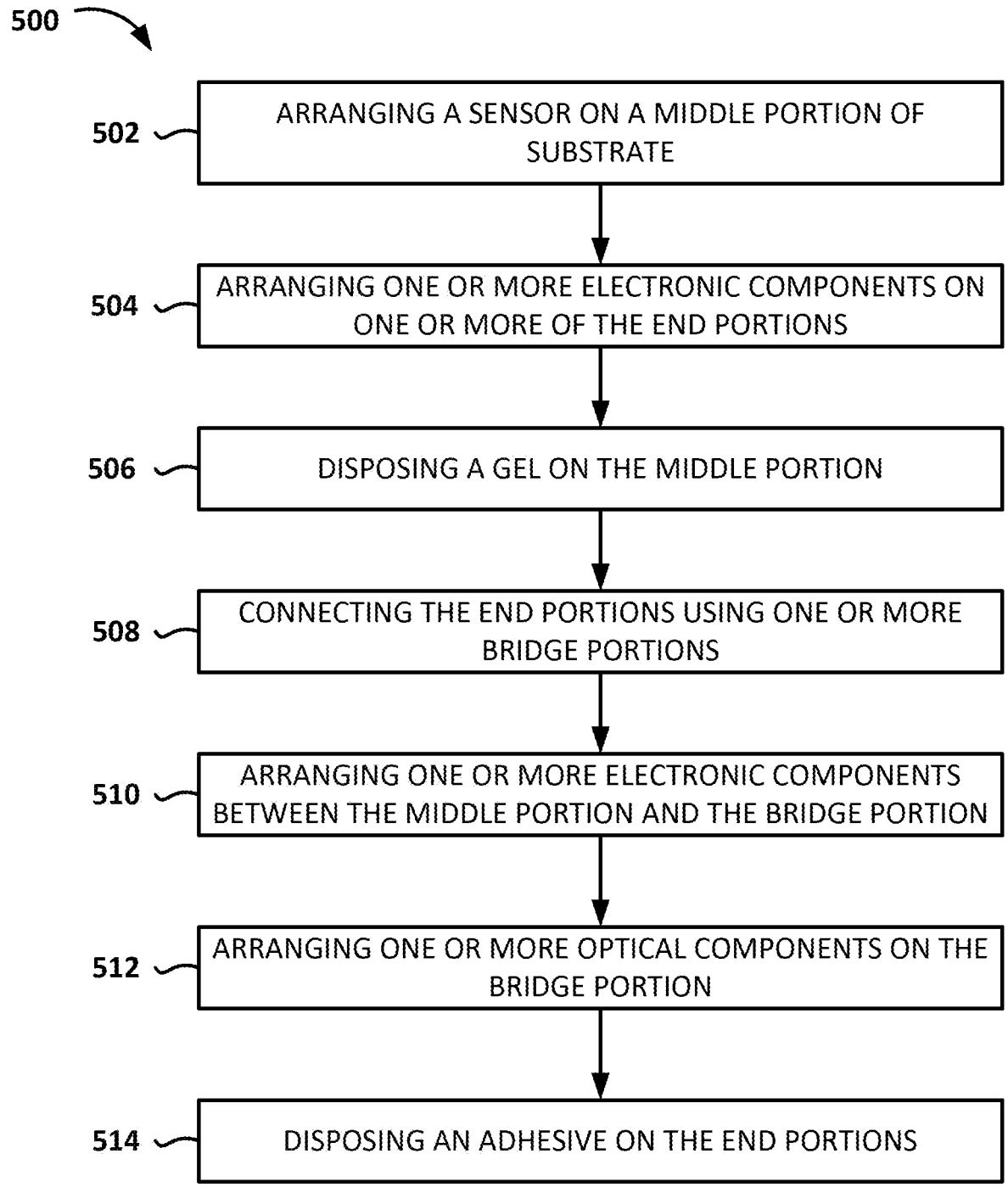
FIG. 5 is a flow diagram illustrating a method of manufacturing a wearable device configured to be attached to a subject, in accordance with embodiments of the disclosure.

FIG. 5 is a flow diagram illustrating a method 500 of manufacturing a wearable device configured to be attached to a subject, in accordance with embodiments of the disclosure. In embodiments, the method 500 may comprise arranging a sensor on a middle portion of substrate (block 502). In embodiments, the sensor may be configured to sense physiological parameters of a subject (e.g., subject 104, subject 314 and/or subject 414) and/or environmental parameters using electrical, mechanical, optical, and/or chemical means. Exemplary physiological parameters may include, but are not limited to: respiratory parameters (e.g., rate, depth, rhythm), motion parameters, (e.g., walking, running, falling, gait, gait rhythm), facial expressions, swelling, heart sounds, sweat, sweat composition (e.g., ammonia, pH, potassium, sodium, chloride), exhaled air composition, Electrocardiography (ECG) parameters, electroencephalogram (EEG) parameters, Electromyography (EMG) parameters, and/or the like. Exemplary environmental parameters may include, but are not limited to: particulates, ultraviolet light, volatile organic compounds, and/or the like in the environment. Additionally or alternatively to arranging a sensor on the middle portion, one or more non-sensor electronic components may be arranged on the middle portion.

In embodiments, the middle portion of the substrate may have the same or similar characteristics as the middle portion 302 and/or the middle portion 402 described above. For example, the middle portion may be arranged between two end portions and the middle portion may be more flexible and/or more stretchable than the end portions.

The method 500 may further comprise arranging one or more electronic components on the end portions (block 504). In embodiments, the one or more electronic components arranged on the end portions may be electrically connected to the sensor arranged on the middle portion. Additionally or alternatively, the one or more electronic components arranged on the end portions may be the same or similar to the electronic components 318B and/or the electronic components 418B. For example, electronic components arranged on the end portions may include, but are not limited to controllers (e.g., controller 208), memory (e.g., memory 210), I/O components (e.g., I/O components 214), communication components (e.g., communication components 216), therapy components (e.g., therapy components 218), transcutaneous members (e.g., transcutaneous members 220), and/or power sources (e.g., power sources 222). In embodiments, the electronic components arranged on the end portions may include processing devices configured to process the sensed parameters of the sensor arranged on the middle portion, memory to store the sensed parameters, transmitters to transmit the sensed parameters, and/or receivers to receive one or more transmissions.

In embodiments, the method 500 may further comprise disposing a gel on the middle portion (block 506). The gel may have the same or similar characteristics as the gel 436 described above.

In embodiments, the method 500 may further comprise connecting the end portions with one or more bridge portions. In embodiments, the one or more bridge portions may have the same or similar characteristics as the bridge portion 320 and/or the bridge portion 420. For example, the bridge portion may be less flexible than the middle portion. As another example, the bridge portion may be arranged distal to and spaced apart from the middle portion. As even another example, the bridge portion may be opaque to one or more types of light. For example, the bridge portion may be opaque to visible light and/or ultraviolet light.

In embodiments, the method 500 may comprise arranging one or more electronic components between the middle portion and the bridge portion (block 510). The one or more electronic components may be the same or similar to the electronic components 418C. For example, the one or more electronic components may be a capacitor that is capable of measuring a pressure on the wearable device.

In embodiments, the method 500 may further comprise arranging one or more optical components on the bridge portion (block 512). The one or more optical components may be the same or similar to the optical 418D discussed above. For example, the one or more optical components may be configured to emit light toward the middle portion and (i) a physiological parameter of the subject and/or (ii) a parameter of the wearable device may be determined based on a reflection portion of the emitted light.

In embodiments, the method 500 may further comprise disposing an adhesive on the end portions (block 514). In embodiments, the adhesive may be the same or similar to the adhesive 316 and/or the adhesive 416.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the presently disclosed subject matter is intended to embrace all such alternatives, modifications, and variations as fall within the scope of the claims, together with all equivalents thereof.

We claim:

1. A wearable device comprising:
a substrate configured to be attached to a subject's skin, the substrate comprising a middle portion arranged between two end portions, wherein the middle portion is thinner than the two end portions such that the middle portion is more flexible than the two end portions, wherein at least the middle portion is stretchable and wherein the thickness of the middle portion is less than or equal to 10 micrometers;
a physiological sensor arranged on the middle portion, the physiological sensor configured to sense a physiological signal of the subject when the wearable device is attached to the subject's skin; and
one or more electrical components arranged on at least one of the end portions,
wherein at least one of the one or more electrical components is coupled to the physiological sensor.

2. The wearable device of claim 1, further comprising a bridge portion connecting the end portions, wherein the bridge portion is less flexible than the middle portion.

3. The wearable device of claim 2, wherein the bridge portion is arranged distal to and spaced apart from the middle portion.

4. The wearable device of claim 3, wherein a gel is arranged between the bridge portion and the middle portion, the gel being configured to facilitate separation between the middle portion and the bridge portion.

5. The wearable device of claim 3, further comprising a capacitor arranged between the bridge portion and the middle portion, the capacitor being configured to measure a pressure on the wearable device, wherein the capacitor includes a first conductive surface arranged on the bridge portion and a second conductive surface arranged on the middle portion.

6. The wearable device of claim 3, wherein the bridge portion is opaque to at least one of visible light and ultraviolet light.

7. The wearable device of claim 3, further comprising one or more optical components arranged on the bridge portion.

8. The wearable device of claim 1, wherein the middle portion is porous to an active pharmaceutical ingredient.

9. The wearable device of claim 1, wherein the middle portion is translucent to light having a wavelength between 600 nanometers and 1000 nanometers.

10. The wearable device of claim 1, wherein an adhesive is disposed on the two end portions but not the middle portion.

11. A method of manufacturing a wearable device configured to be attached to a subject's skin, the method comprising:
- arranging a physiological sensor on a middle portion of a substrate, wherein the middle portion is between end portions of the substrate that are thicker than the middle portion, the middle portion of the substrate being more flexible than at least one of the end portions and the physiological sensor configured to sense a physiological signal of the subject when the wearable device is attached to the subject's skin;
- arranging one or more electrical components on at least one of the end portions, wherein at least one of the one or more electrical components are electrically connected to the physiological sensor;
- connecting the end portions using a bridge portion that is less flexible than the middle portion; and
- disposing a gel on the middle portion, the gel being configured to facilitate separation between the middle portion and the bridge portion.

12. The method of claim 11, wherein the bridge portion is arranged distal to and spaced apart from the middle portion.

13. The method of claim 11, further comprising arranging a capacitor between the bridge portion and the middle portion, the capacitor being configured to measure a pressure on the wearable device, wherein the capacitor includes a first conductive surface arranged on the bridge portion and a second conductive surface arranged on the middle portion.

14. The method of claim 11, wherein the bridge portion is opaque to at least one of visible light and ultraviolet light.

15. The method of claim 11, further comprising disposing an adhesive on the end portions but not the middle portion.

16. The method of claim 11, further comprising arranging one or more optical components on the bridge portion.

17. A wearable device comprising:
- a substrate configured to be attached to a subject's skin, the substrate comprising a middle portion arranged between two end portions, wherein the middle portion is thinner than the two end portions such that the middle portion is more flexible than the two end portions, wherein at least the middle portion is stretchable;
- a bridge portion connecting the end portions and arranged distal to and spaced apart from the middle portion;
- a capacitor arranged between the bridge portion and the middle portion, the capacitor being configured to measure a pressure on the wearable device, wherein the capacitor includes a first conductive surface arranged on the bridge portion and a second conductive surface arranged on the middle portion;
- a physiological sensor arranged on the middle portion, the physiological sensor configured to sense a physiological signal of the subject when the wearable device is attached to the subject's skin; and
- one or more electrical components arranged on at least one of the end portions,
- wherein at least one of the one or more electrical components is coupled to the physiological sensor.

18. The wearable device of claim 17, wherein a gel is arranged between the bridge portion and the middle portion, the gel being configured to facilitate separation between the middle portion and the bridge portion.

19. The wearable device of claim 17, wherein the bridge portion is opaque to at least one of visible light and ultraviolet light.

20. The wearable device of claim 17, wherein the middle portion is translucent to light having a wavelength between 600 nanometers and 1000 nanometers.

* * * * *